United States Patent
Fogarty

(10) Patent No.: US 8,617,052 B2
(45) Date of Patent: Dec. 31, 2013

(54) PENILE PROSTHETIC SYSTEM AND PUMP HAVING INLET VALVE WITH HIGH VELOCITY CLOSURE MECHANISM

(75) Inventor: Terence M. Fogarty, Hudson, WI (US)

(73) Assignee: Coloplast A/S, Humlebaek (DK)

( * ) Notice: Subject to any disclaimer, the term of this patent is extended or adjusted under 35 U.S.C. 154(b) by 0 days.

(21) Appl. No.: 13/564,723

(22) Filed: Aug. 2, 2012

(65) Prior Publication Data

US 2012/0296158 A1 Nov. 22, 2012

Related U.S. Application Data

(63) Continuation of application No. 13/306,993, filed on Nov. 30, 2011, now Pat. No. 8,257,246.

(60) Provisional application No. 61/476,765, filed on Apr. 19, 2011.

(51) Int. Cl.
*A61F 5/00* (2006.01)

(52) U.S. Cl.
USPC .......................................................... 600/40

(58) Field of Classification Search
USPC ...................................................... 600/38–41
See application file for complete search history.

(56) References Cited

U.S. PATENT DOCUMENTS

| 7,918,782 | B2 * | 4/2011 | George et al. | ................... | 600/40 |
| 2007/0142700 | A1 * | 6/2007 | Fogarty et al. | ................... | 600/40 |

* cited by examiner

*Primary Examiner* — Samuel Gilbert
(74) *Attorney, Agent, or Firm* — Coloplast Corp., Coloplast A/S; Nick Baumann

(57) ABSTRACT

A pump connected to a reservoir and a cylinder of an implantable penile prosthesis includes a pump body and an inlet valve assembly. The pump body has a pump bulb connected to the pump body, where the pump bulb is operable to move fluid between the reservoir and the cylinder. The inlet valve assembly includes a valve and a tubular sleeve that provides an exit valve seat. The inlet valve assembly is disposed in an inlet channel of the pump body and operable to allow a portion of fluid to be drawn from the reservoir through the tubular sleeve and through the inlet channel to the pump bulb for delivery into the cylinder.

14 Claims, 9 Drawing Sheets

PENILE PROSTHETIC SYSTEM AND PUMP HAVING INLET VALVE WITH HIGH VELOCITY CLOSURE MECHANISM

BACKGROUND

An implanted penile prosthetic is a proven approach to relieve erectile dysfunction for male users.

A penile prosthetic typically includes one or more cylinders that are implanted in the corpora cavernosa of the penis, a reservoir implanted in the abdomen that communicates with the cylinder(s), and a pump, often located in the scrotum, that is employed to move liquid from the reservoir into the cylinder(s).

In a typical application, the user squeezes a bulb of the pump multiple times to draw liquid out of the reservoir into the bulb and thereafter transfer the liquid from the bulb into the cylinder(s). Squeezing the bulb thus inflates the cylinder(s) to provide the user with an erect penis. The user may return the penis to its flaccid state by selectively activating a deflation mechanism and transferring the liquid from the cylinder(s) back into the reservoir.

It is desirable to provide the user with a simple mechanism for deflation of the cylinders. However, the cylinders are typically inflated to a pressure of several pounds-per-square-inch (psi) or greater and the resultant high pressure deflation of the cylinders has the potential to undesirably close the deflation mechanism.

SUMMARY

One aspect provides a pump connected to a reservoir and a cylinder of an implantable penile prosthesis. The pump includes a pump body and a pump bulb that is connected to the pump body, an inlet valve assembly, and an exhaust valve assembly. The pump bulb is operable to move fluid between the reservoir and the cylinder. The inlet valve assembly includes a valve and a tubular sleeve that provides an exit valve seat. The inlet valve assembly is disposed in an inlet channel of the pump body and is operable to allow a portion of fluid to be drawn from the reservoir through the tubular sleeve and through the inlet channel for delivery into the pump bulb. The exhaust valve assembly is disposed in the pump body and is operable to allow the portion of the fluid delivered into the pump bulb to be moved into the cylinder. The valve in one embodiment is an inlet valve that is movable to contact the exit valve seat and prevent fluid that is flowing from the cylinder to the reservoir from flowing through the inlet channel.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

Figure 1:
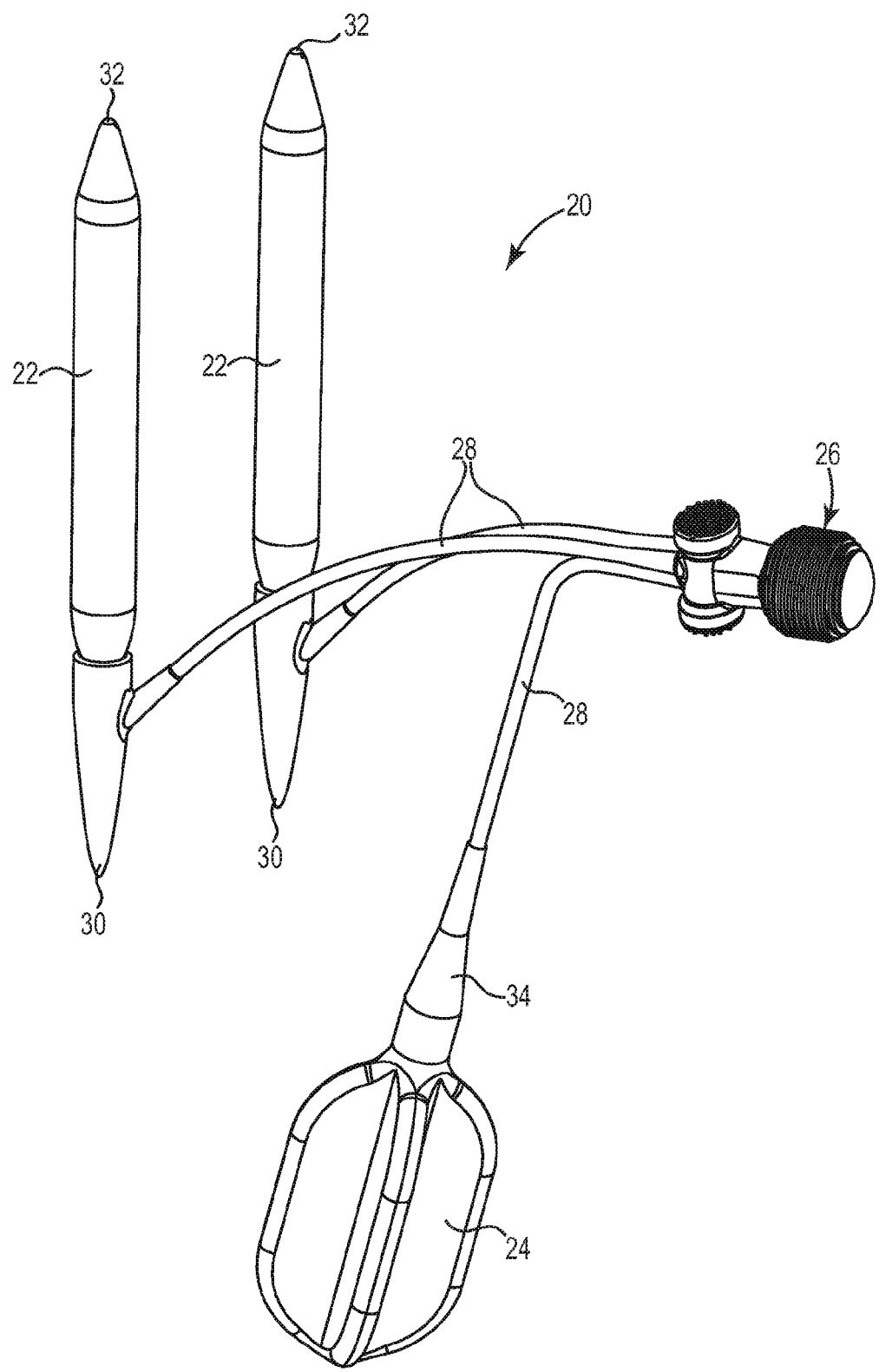
FIG. 1 is a perspective view of one embodiment of a penile prosthetic that includes cylinders for implantation into the penis, a reservoir, and a pump connected to the cylinders and the reservoir.

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

It is to be understood that the features of the various exemplary embodiments described herein may be combined with each other, unless specifically noted otherwise.

The term "proximal" as employed in this application means that part that is nearest the body of the user. The term "distal" as employed in this application means that part that is farthest from the body of the user. A distal end is the furthest endmost location of a distal portion of a thing being described, whereas a proximal end is the nearest endmost location of a proximal portion of the thing being described.

"Autoinflation" means an involuntary inflation of a cylinder implanted in a penis. Autoinflation occurs when the pressure of the liquid inside a reservoir that supplies the cylinder is increased, and the increased pressure forces liquid from the reservoir into the cylinder. The consequence is an unintended and undesirable erection of the penis. In one embodiment, the pump disclosed herein includes an anti-autoinflation (AAI) mechanism that is disposed in the pump body and has a seal that is biased to prevent fluid flow from bypassing the pump bulb and flowing directly from the reservoir to the cylinders.

Embodiments provide a penile prosthetic including a pump having a one touch release mechanism that maintains a deflation valve of the pump in an open position during device deflation. Some users operate their penile prosthesis at a "high" cylinder pressure (about 50 psi, with pressure excursions reaching as high as 75 psi) and the deflation valve should remain open at these high pressures to maintain the one touch release feature of the deflation valve. During device deflation, fluid returns from the inflatable penile cylinders through the pump body to the fluid reservoir. If the penile cylinders are highly pressurized, the fluid flowing from the two cylinder tubes through a single tube leading to the reservoir can create a flow restriction and give rise to fluid flow through the inlet and exhaust valves, which can undesirably close the deflation valve and interrupt device deflation.

Embodiments provide a pump having a mechanism that prevents high pressure fluid (e.g., above about 8 psi) or high velocity fluid from closing the deflation valve during device deflation. The pump has an inlet valve assembly including a valve that is biased into contact with an entry valve seat of an inlet channel by a spring. The valve is movable a small distance to allow fluid to be drawn from the reservoir, through the inlet valve assembly, and into the pump bulb. However, movement of the valve is restricted. For example, in the presence of a high pressure fluid flow the valve moves a distance and seals against an exit valve seat inside the inlet channel to prevent fluid that is flowing from the cylinder to the reservoir from flowing through the inlet channel. Thus, the inlet valve has two seats, and the exit valve seat provides the inlet valve assembly with a high velocity closure mechanism that is configured to block the inlet channel during high-pressure deflation of the cylinders. The inlet valve assembly thus prevents flow restrictions and/or pressure excursions that can lead to the undesirable closing of the deflation valve during device deflation.

FIG. 1 is a perspective view of one embodiment of a penile prosthetic 20. The penile prosthetic 20 includes cylinders 22 for implantation into a penis, a reservoir 24, and a pump 26 connected to the cylinders 22 and the reservoir 24, for example by kink resistant tubing 28.

Each of the cylinders 22 includes a proximal end 30 opposite a distal end 32. During implantation, the proximal end 30 (also called a rear tip) is implanted toward the crus of the penis and the distal end 32 is implanted within the glans penis. The cylinders 22 are fabricated from material configured to collapse and be flexible when the cylinders 22 are deflated to provide the penis with a flaccid state and expand when the cylinders 22 are inflated with fluid to provide the penis with an erection. As a point of reference, the cylinders 22 of FIG. 1 are illustrated in an inflated state. Suitable material for fabricating the cylinders 22 includes silicone, biocompatible polymers such as urethanes, blends of polymers with urethane, copolymers of urethane, or the like. Suitable cylinders are available from Coloplast Corp., Minneapolis, Minn.

The reservoir 24 is sized to maintain a volume of liquid between about 50-300 ml and includes a neck 34 that is smoothly coupled with the kink resistant tubing 28. In one embodiment, the reservoir 24 is provided as a "cloverleaf" style of reservoir having multiple leaves that may be folded one against the other to compact the reservoir 24 for implantation into the abdomen of the user. One suitable reservoir 24 is sized to retain approximately 130 mL of liquid and is available from Coloplast Corp., Minneapolis, Minn.

Figure 2:
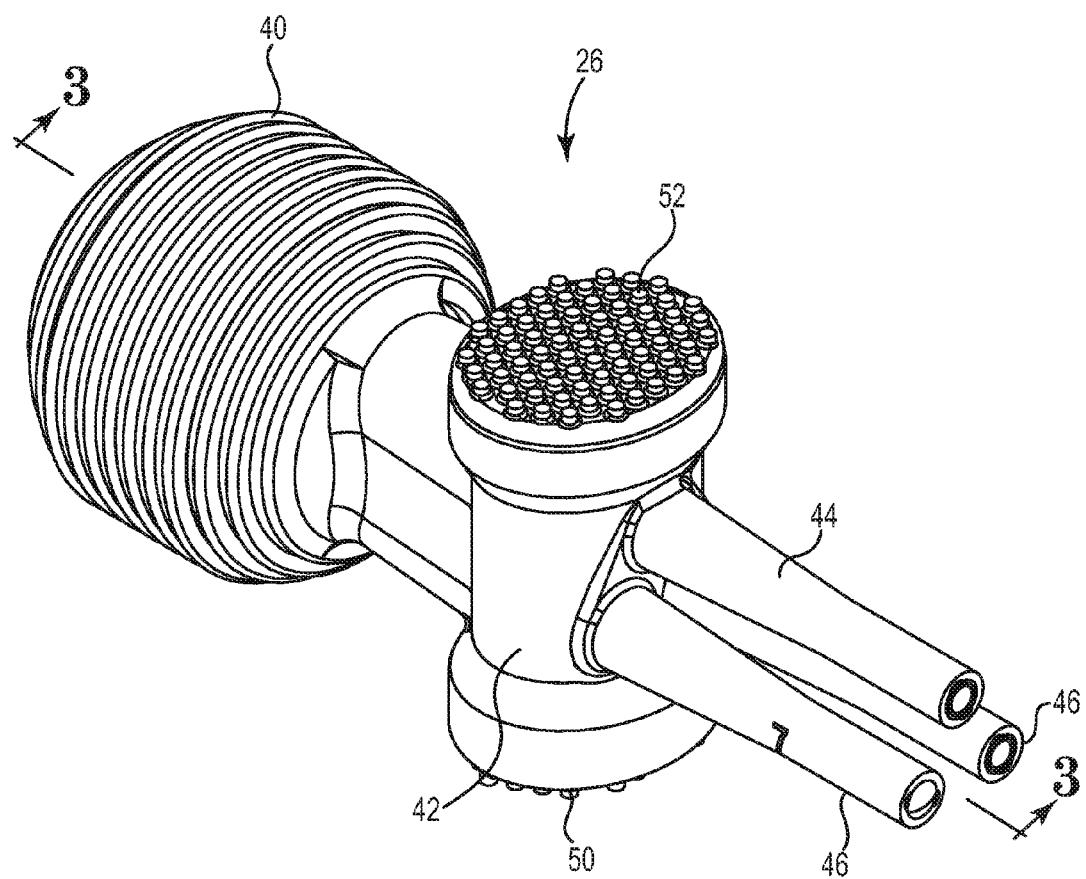
FIG. 2 is a perspective view of the pump illustrated in FIG. 1.

FIG. 2 is a perspective view of the pump 26. The pump 26 includes a pump bulb 40, a pump body 42, an inlet tube 44 connected with the pump body 42, and a pair of exhaust tubes 46 extending from the pump body 42.

In one embodiment, the pump bulb 40 is flexible and includes a ribbed accordion structure that allows the pump bulb 40 to collapse to drive liquid out of the pump bulb 40, through the pump body, and out of the exhaust tubes 46. The pleated accordion structure is configured to recover to expand the bulb 40, which creates a negative local pressure in the bulb 40 that draws liquid out of the reservoir 24 (FIG. 1), through the inlet tube 44 and the pump body 42, and into the pump bulb 40.

In one embodiment, the pump body 42 is integrally formed and connected with the pump bulb 40 and includes a first activation surface 50 opposite a second activation surface 52. The activation surfaces 50, 52 (also called deflate pads) are illustrated as non-circular (elliptical) although other shapes for the activation surfaces 50, 52 are also acceptable. The pump body 42 houses or maintains valves (described below) that may be activated/deactivated by pressing the activation surfaces 50, 52.

The inlet tube 44 is connected to the reservoir 24 (FIG. 1) by the kink resistant tubing 28. Each of the exhaust tubes 46 is connected to a respective one of the cylinders 22 via the kink resistant tubing 28. Compressing the pump bulb 40 ejects the liquid from the bulb 40 through the exhaust tubes 46 to the cylinders 22, and expansion of the pump bulb 40 creates suction that draws liquid from the reservoir 24 through the pump body 42 and the inlet tube 44 at a low velocity for delivery into the pump bulb 40.

Generally, the pump 26 is implanted into the scrotum of the user and connected to the cylinders 22 that are implanted into the penis of the user and the reservoir 24 that is implanted within the abdomen of the user. The pump 26 is fabricated from material suitable for body implantation, such as silicone or the urethane-based materials described above for the cylinders 22 or the reservoir 24.

Figure 3:
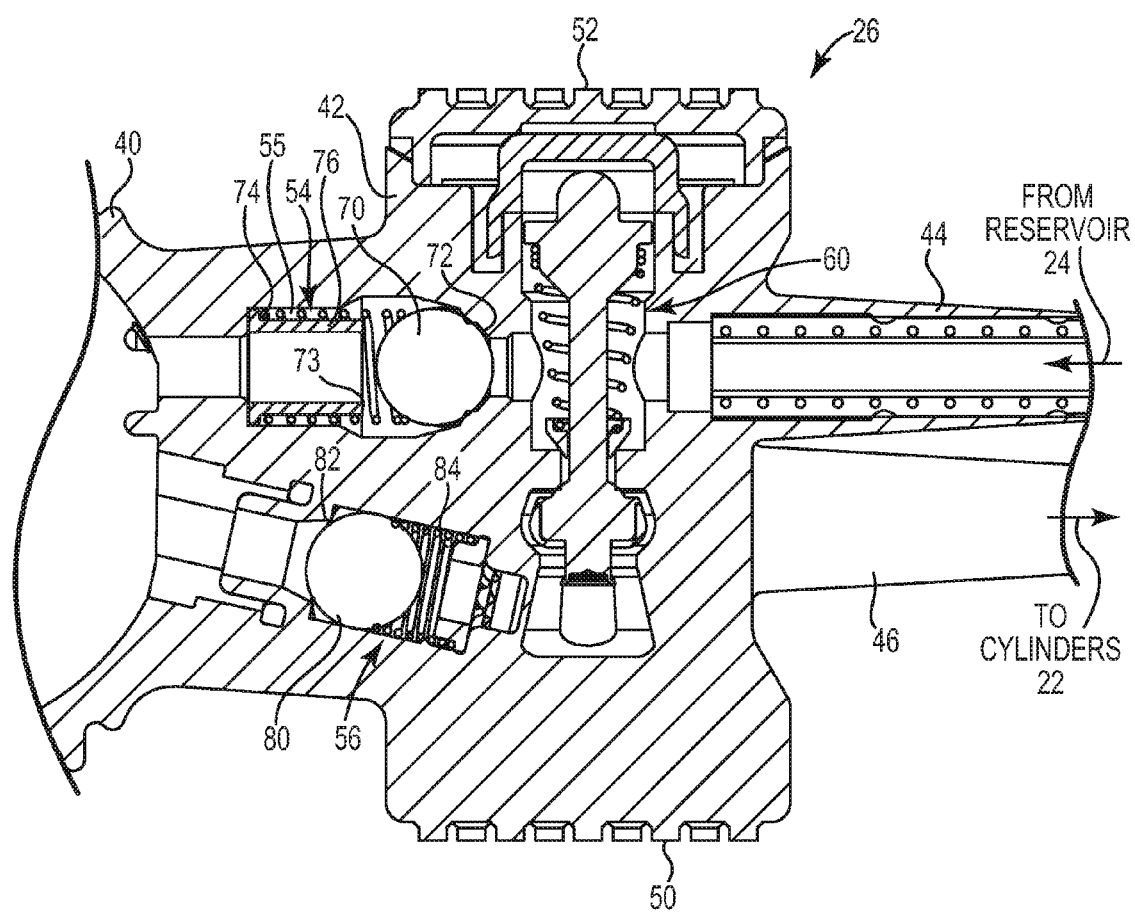
FIG. 3 is a cross-sectional view of a pump body of the pump illustrated in FIG. 2 including an inlet valve provided with a tubular sleeve.

FIG. 3 is a cross-sectional view of the pump 26. The pump 26 includes an inlet valve assembly 54 disposed in an inlet channel 55 of the pump body 42 that communicates between the reservoir 24 and the pump bulb 40, an exhaust valve assembly 56 disposed within the pump body 42 that communicates between the pump bulb 40 and the cylinders 22, and deflation valve 60. In one embodiment, the deflation valve 60 is disposed in the pump body 42 transversely between the inlet valve assembly 54 and the exhaust valve assembly 56. In one embodiment, the deflation valve 60 is configured as an anti-autoinflation (AAI) valve providing the structure and function described below.

In one embodiment, the inlet valve assembly 54 includes a valve 70 that is biased by a spring 74 for contact with an entry valve seat 72, or alternatively with an exit valve seat 73 provided by a tubular sleeve 76. The tubular sleeve 76 is axially aligned with the spring 74. The valve 70 is thus provided with two seats 72, 73. The exit valve seat 73 provides the inlet valve assembly 54 with a high velocity closure mechanism that is configured to block the inlet channel 55 during high-pressure deflation of the cylinders 22.

Suitable valves 70 include ball valves, poppet valves, and flexible disk valves such as a rubber flap style of valve.

In one embodiment, the valve 70 is biased by the spring 74 into contact or near-contact with the entry valve seat 72 to define a closed position of the inlet valve assembly 54 that is configured to allow the pump bulb 40 to eject liquid out of the bulb 40 into the cylinders 22.

In one embodiment, the valve 70 is biased off of the entry valve seat 72 to define an open position of the inlet valve assembly 54 that is configured to allow the pump bulb 40 to draw fluid out of the reservoir 24 and into the bulb 40 for subsequent ejection into the cylinders 22. For example, during inflation and rebound of the bulb 40, the inlet valve 70 that was biased to the closed position moves to an open position.

In one embodiment, high velocity fluid flow of fluid that is flowing from the cylinders 22 to the reservoir 24 moves the valve 70 into contact with the exit valve seat 73 to substantially and effectively close the inlet channel 55 and prevent fluid that is flowing from the cylinders 22 to the reservoir 24 from flowing through the inlet channel 55.

During device inflation, the valve 70 is configured to be displaced a small distance from the entry valve seat 72 (thus compressing the spring 74) to allow a portion of the fluid volume in the reservoir 24 to be drawn through the inlet tube 44, around or past the valve 70 through the inlet channel 55, and into the pump bulb 40. When the liquid flow from the reservoir 24 is reduced, or more specifically, when the pressure driving the liquid flow from the reservoir 24 is reduced, the spring 74 biases the valve 70 into contact with the entry valve seat 72 to seat the valve 70 on the entry valve seat 72 and block backflow of the liquid from the bulb 40 back to the reservoir 24. In this manner, the inlet valve assembly 54 is provided as a one-way inlet valve.

During device deflation, and in particular during device deflation in the presence of a flow of "high pressure" liquid above about 8 psi, the exit valve seat 73 of the tubular sleeve 76 receives the valve 70 to effectively block the flow of liquid through the inlet channel 55. Thus, although the high-pressure liquid might displace the valve 70 away from the entry valve seat 72, the tubular sleeve 76 limits the movement of the valve 70 and provides a high velocity closure mechanism for the inlet valve assembly 54. In one embodiment, the tubular sleeve 76 of the inlet valve assembly 54 provides the pump 26 with means for preventing the fluid flowing from the cylinders 22 to the reservoir 24 from closing the deflation valve 60.

The exhaust valve assembly 56 includes a valve 80 that is biased into contact with a surface 82 by a spring 84. The valve 80 is configured to be displaced from the surface 82 (thus compressing the spring 84) when liquid flows from the pump bulb 40 through the exhaust valve assembly 56 toward the cylinders 22. For example, compressing the pump bulb 40 ejects liquid from the pump bulb 40, which unseats the valve 80 from the surface 82 to allow the liquid to flow past the valve 80 and the deflation valve 60 into the cylinders 22. The expansion (or recovery) of the pump bulb 40 will draw liquid from the reservoir 24, past the valve 70, and into the bulb 40. Subsequent pumping of the bulb 40 ejects the fluid from the bulb 40 into the cylinders 22. The spring 84 biases the valve 80 into contact with the surface 82 to block backflow of liquid from the cylinders 22 into the pump bulb 40. In this manner, the exhaust valve assembly 56 is provided as a one-way exhaust valve.

Figure 6:
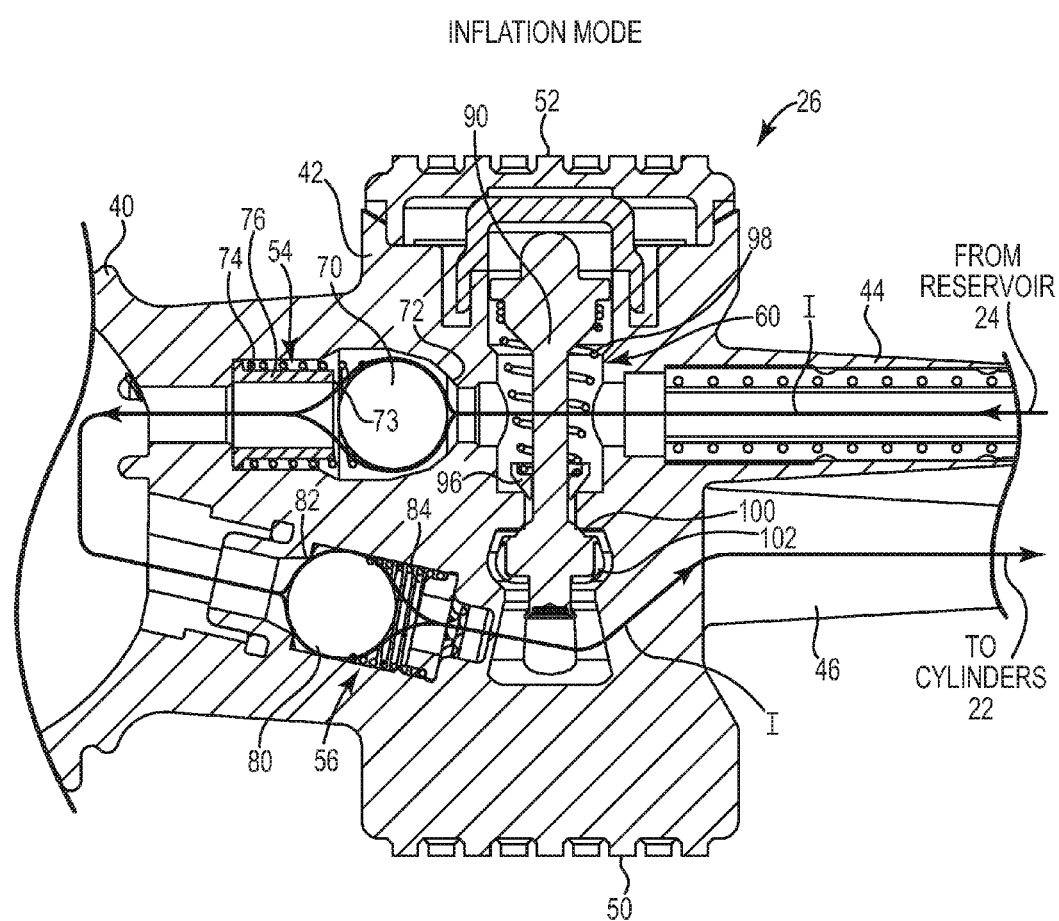
FIG. 6 is a cross-sectional view of the pump body configured for inflation of the cylinders.

In one embodiment, the pump body 42 is an elastomeric chamber molded around the deflation valve 60. The deflation valve 60 is configured to allow liquid to flow from the reservoir 24 into the pump bulb 40 and out the pump bulb 40 into the cylinders 22 during inflation of the cylinders (FIG. 6). The deflation valve 60 is also configured to allow for the rapid deflation of the cylinders 22 (FIG. 6). For example, in one embodiment pressing on the activation surfaces 50, 52 positions the deflation valve 60 to allow fluid to flow from the cylinders 22 through the pump body 42, bypassing the pump bulb 40, and flowing directly back into the reservoir 24, as described below. In addition, the deflation valve 60 is configured to prevent undesirable autoinflation of the cylinders 22 by preventing fluid from flowing from the reservoir 24 directly into the cylinders 22, through the deflation valve 60, as also described below.

Figures 4A, 4B:
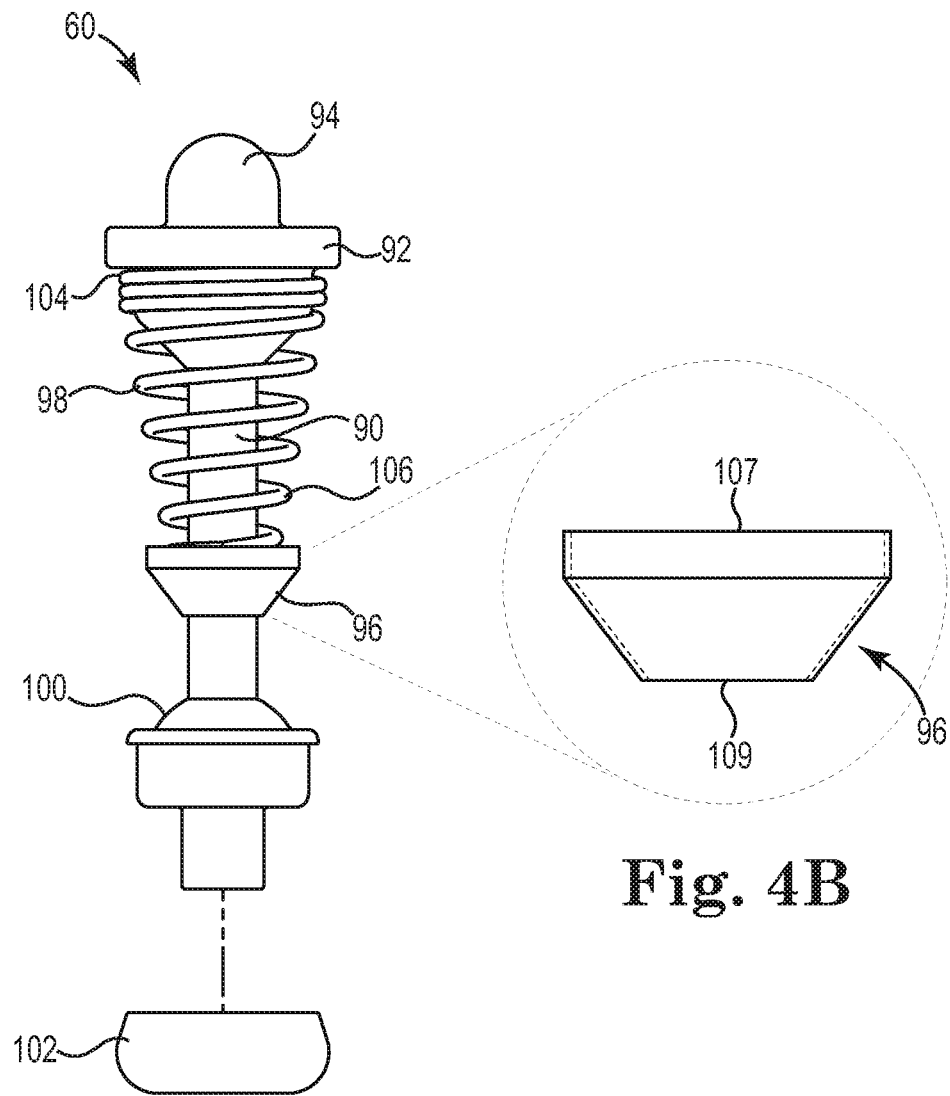
FIG. 4A is a side view of one embodiment of a deflation valve provided in the pump.
FIG. 4B is a side view of a seal of the deflation valve illustrated in FIG. 4A.

FIG. 4A is a side view of the deflation valve 60. The deflation valve 60 includes a valve stem 90, a flange 92 disposed on a first end of portion 94 of the valve stem 90, a seal 96, a spring 98 that biases the seal 96 away from the flange 92 toward a second end portion 100 of the valve stem 90, and a crown 102 attached to the valve stem 90 opposite the flange 92. In one embodiment, the spring 98 is a conical spring having a base 104 that interacts with the flange 92 and an end 106 that interacts with the seal 96. The base 104 is wider than the end 106.

FIG. 4B is a side view of the seal 96. In one embodiment, the seal 96 is a conical seal having a wider end 107 oriented toward the flange 92 and a narrower end 109 oriented toward the second end portion 100. The conical spring 98 is mated into the wider conical end 107 of the seal 96. The wider end 107 is configured to block or deny the flow of liquid from the reservoir 24 transverse through the pump body 42 into the cylinders 22.

With reference to FIG. 3, in one embodiment the deflation valve 60 provides an anti-autoinflation (AAI) valve in which the wider end 107 of the seal 96 of the deflation/AAI valve 60 is configured to be biased by the spring 98 to prevent fluid flow from flowing through the deflation valve 60 directly from the reservoir 24 into the cylinders 22 through the pump body 42. Any fluid that flows from the reservoir 24 through the pump body 42 toward the exhaust tubes 46 (i.e., autoinflation flow) forces the wider end 107 of the seal 96 toward the second end portion 100 of the valve stem 90 to close off the flow path in the direction of the exhaust tubes 46. In one embodiment, the second end portion 100 of the valve stem 90 seals the flow path through the pump body 42 during inflation of the cylinders 22 to prevent fluid that is flowing from the pump bulb 40 from being diverted through the pump body 42 to or toward the reservoir 24.

Figure 5A:
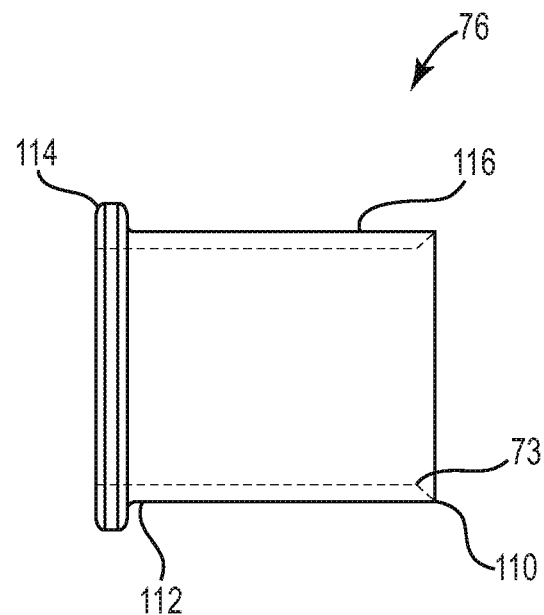
FIG. 5A is a side view of the tubular sleeve illustrated in FIG. 3.
Figure 5B:
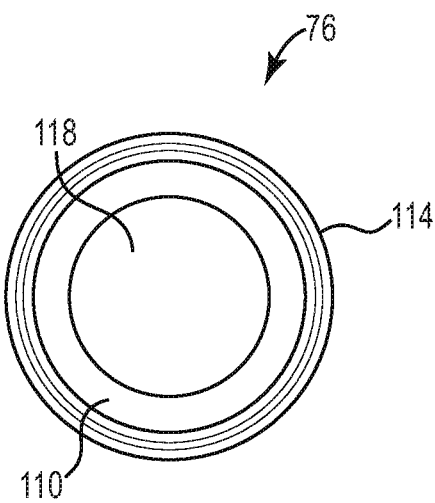
FIG. 5B is a distal end view of the tubular sleeve illustrated in FIG. 3.

FIG. 5A is a side view and FIG. 5B is an end view of the tubular sleeve 76. The tubular sleeve 76 includes a distal end 110 providing the exit valve seat 73 that is configured to seal against the valve 70 and a proximal end 112 that includes a flange 114 that extends in a radial direction away from a wall 116 of the tubular sleeve 76. In one embodiment, the distal end 110 provides an exit valve seat configured to receive and seal with the valve 70. With reference to FIG. 3, the valve 70 thus moves between a first closed position in which the valve 70 is closed against the entry valve seat 72 as fluid is ejected from the bulb 40 into the cylinders 22, an open position in which the valve 70 is between the entry valve seat 72 and the exit valve seat 73 to allow fluid to flow from the reservoir 24 into the bulb 40, and a second closed position in which the valve 70 is closed against the exit valve seat 73 to prevent fluid that is flowing from the cylinders 22 to the reservoir 24 from flowing through the inlet channel 55.

In one embodiment, the tubular sleeve 76 provides a through-opening 118 that is configured to allow low-pressure and low-velocity fluid to flow through the tubular sleeve 76 and the inlet channel 55, for example during inflation of the cylinders 22. With additional reference to FIG. 3, the flange 114 is sized for placement between a wall of the inlet channel 55 and the spring 74. In one embodiment, the tubular sleeve 76 is placed such that the wall 116 is inside the spring 74. In one embodiment, the tubular sleeve 76 is placed such that the wall 116 is outside the spring 74.

In one embodiment, the tubular sleeve is fabricated from stainless steel and includes the following exemplary dimensions: the wall 116 is provided with an inside diameter of about 0.095 inches and an outside diameter of about 0.130 inches; the sleeve 76 has a length of about 0.165 inches; the outside diameter of the flange 114 is about 0.156 inches; and a thickness of the flange is about 0.015 inches, although other dimensions are acceptable.

FIG. 6 is a cross-sectional view of the pump 26 with the deflation valve 60 configured for inflation of the cylinders 22 (i.e., deflation valve is in the inflation mode). When at rest, the valve 70 is biased onto the entry valve seat 72 by the spring 74 and the valve 80 is biased onto the sealing surface 82 by the spring 84. With additional reference to FIG. 1, when the pump bulb 40 expands to create a vacuum, fluid is drawn from the reservoir 24 across the pump body 42 and into the pump bulb 40. The fluid moves through the inlet tubing 44 and through the inlet valve assembly 54 along a pathway I. The valve 70 is displaced from the entry valve seat 72 to allow the fluid to flow around the valve 70 and through the inlet valve assembly 54 into the pump bulb 40. When the pump bulb 40 is compressed, the fluid in the pump bulb 40 flows through the exhaust valve assembly 56 along the pathway I, displacing the valve 80 away from its seat on a surface 82. The fluid is ejected from the pump bulb 40 and flows along the pathway I around the crown 102 of the deflation valve 60, through the exhaust tubing 46 and to the cylinders 22.

In one embodiment, the inlet valve assembly 54 is aligned with the pump bulb 40 and the inlet tubing 44, and the exhaust valve assembly 56 is aligned with the pump bulb 40 and the exhaust tubing 46.

In one embodiment, when the pump bulb 40 is squeezed, fluid moving through the exhaust valve assembly 56 forces the deflation valve 60 upward to seal the deflation valve 60 and prevent the fluid that is flowing toward the cylinders 22 from being diverted through the pump body 42 toward the reservoir 24. Subsequent multiple pumps of the pump bulb 40 transfers the fluid in the reservoir 24 through the pump body 42, to the pump bulb 40, and out of the pump bulb 40 to the cylinders 22.

The deflation valve 60 is placed within the pump body 42 transverse relative to the fluid pathway I. During inflation, both the inlet valve assembly 54 and the deflation valve 60 close to prevent the fluid flowing from the pump bulb 40 to the cylinders 22 from being diverted back toward the reservoir 24. Specifically, in one embodiment the second end portion 100 of the valve stem 90 provides a deflate valve that is configured to prevent fluid from flowing toward the reservoir 24 during inflation of the cylinders 22. In some cases, the deflation valve 60 is configured to have an open state associated with the rapid deflation of the cylinders 22. In the open state, a first compression of the pump bulb 40 ejects fluid from the pump bulb 40 that impinges on the crown 102 and the deflation valve 60 to close the deflation valve 60. In one embodiment, the deflation valve 60 is a multi-functional valve that prevents flow to the reservoir 24 during cylinder inflation.

In one embodiment, the inlet valve assembly 54 is minimally biased in the closed position so that it can open to allow fluid flow from the reservoir 24 to the pump bulb 40 as the pump bulb 40 rebounds. Pump bulb rebound causes a negative pressure on the inlet valve assembly 54, usually less than 10 inches of mercury. The inlet valve assembly 54 can open fully at negative pressures less than 10 inches of mercury. The inlet valve 70 cooperates with the entry valve seat 72 to prevent fluid from returning to the reservoir 24 when the pump bulb 40 is collapsed. In one embodiment, the inlet valve spring 74 is sized so that the inlet valve assembly 54 remains open at low pressure (<10 inches of mercury).

Figure 7:
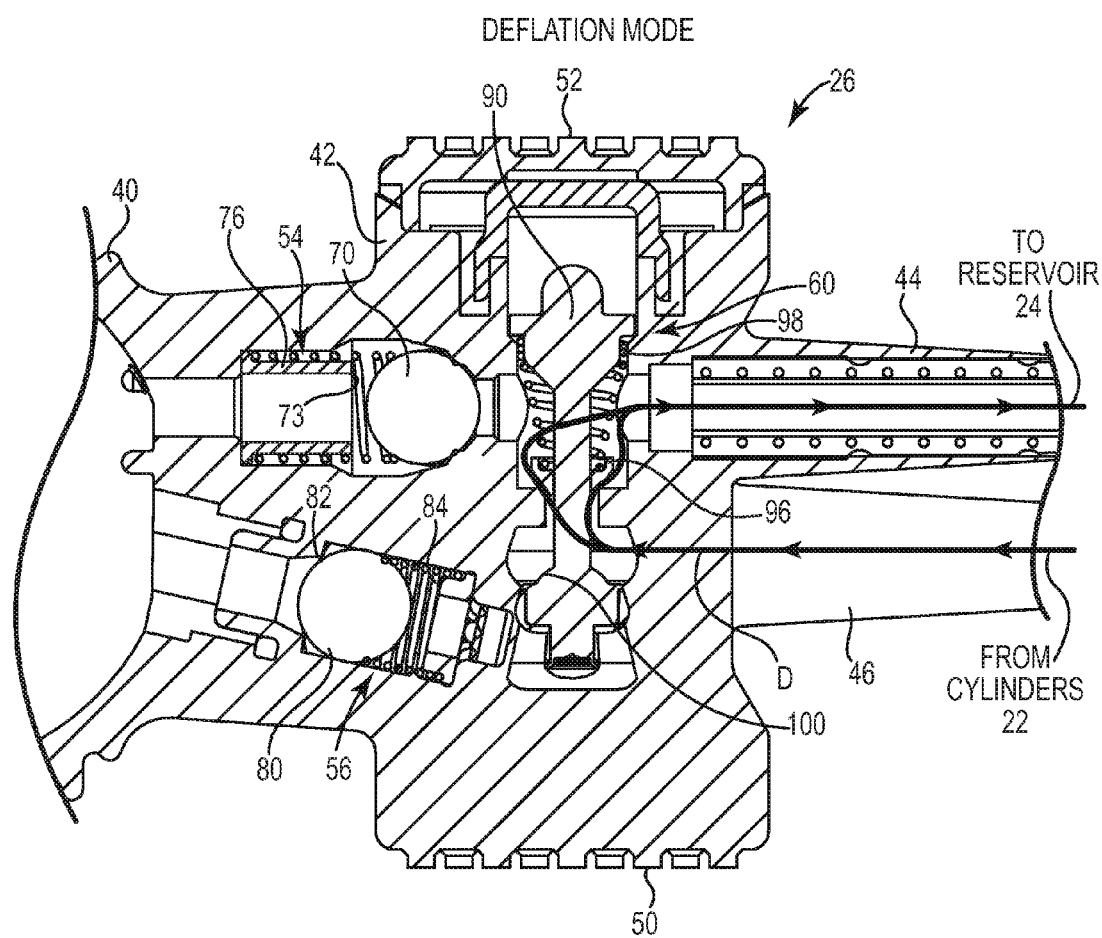
FIG. 7 is a cross-sectional view of the pump body with the deflation valve configured for deflation of the cylinders.

FIG. 7 is a cross-sectional view of the pump 26 with the deflation valve 60 configured for deflation of the cylinders 22 (i.e., valve 60 is in the deflation mode). The deflation valve 60 allows for the rapid deflation of the cylinders 22 by providing a pathway D from the cylinders 22 back to the reservoir 24 that bypasses the pump bulb 40. In one embodiment, the activation surfaces 50, 52 are pressed to allow the fluid flow to dislodge the seal 96 from its seat inside of the pump body 42. Dislodging the seal 96 provides the liquid in the cylinders 22 with the pathway D through the pump body 42 that bypasses the pump bulb 40. The exhaust valve assembly 56 seals the flow path between the cylinders 22 and the pump bulb 40 during deflation of the cylinders 22 to ensure that the fluid being forced from the cylinders 22 is diverted through the pump body 42 (away from the pump bulb 40) and back into the reservoir 24. When the activation surfaces 50, 52 are pressed, the seal 96 is displaced upward from the flow of fluid (relative to the illustration of FIG. 6) to compress the spring 98 and allow fluid to move past the seal 96 along the pathway D and back to the reservoir 24. The valve 80 is seated against the surface 82 to prevent fluid flowing from the cylinders 22 back into the pump bulb 40. Thus, the path of least resistance for fluid leaving the cylinders 22 is across the unseated seal 96.

Figure 8:
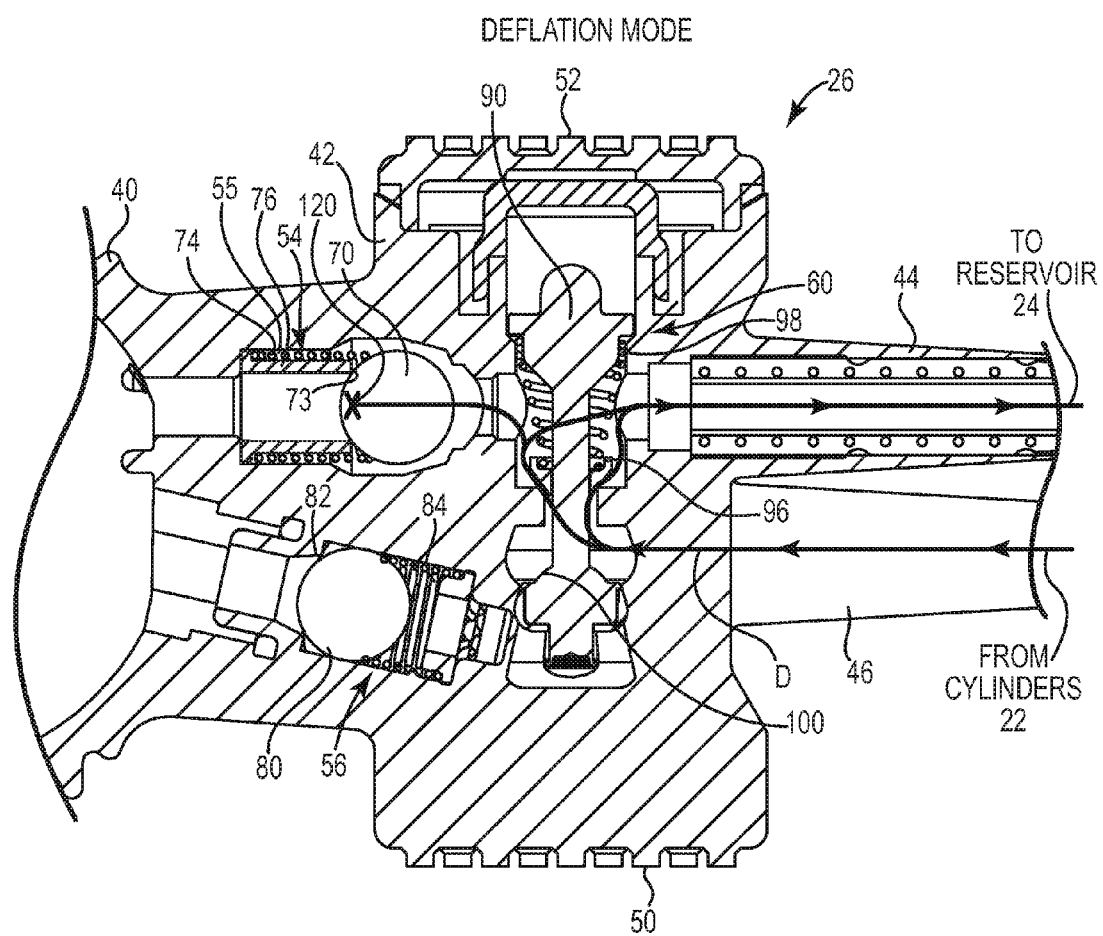
FIG. 8 is a cross-sectional view of the pump body in a deflation mode where the tubular sleeve illustrated in FIG. 3 prevents pressurized fluid flowing from the cylinders back to the reservoir from creating a pressure situation that could potentially close the deflation valve.

FIG. 8 is a cross-sectional view of the pump 26 with the deflation valve 60 deflation mode in the presence of high-pressure fluid flowing from the cylinders 22 back to the reservoir 24. The high-pressure fluid flows along pathway D through the pump body 42. The tubular sleeve 76 is positioned to receive the valve 70 and prevent the high-pressure fluid from diverting through the inlet valve assembly 54 and flowing through the inlet channel 55, which is a condition that can give rise to fluid recirculation through the inlet valve assembly 54, pump bulb 40, and exhaust valve 56 that will result in closing of the deflation valve 60. For example, the high-pressure fluid is stopped at location 120 as the valve 70 seats against the tubular sleeve 76. The high-pressure fluid continues along the fluid pathway D into the reservoir 24.

Some physical activities can lead to the compression or pressurization of the reservoir 24. High reservoir pressure has the potential to cause fluid to flow from the reservoir 24 through the pump body 42 directly into the cylinders 22, potentially causing undesired autoinflation of the cylinders 22. In one embodiment, the deflation valve 60 is configured to incorporate an AAI valve 60 that prevents autoinflation of the cylinders 22.

Figure 9:
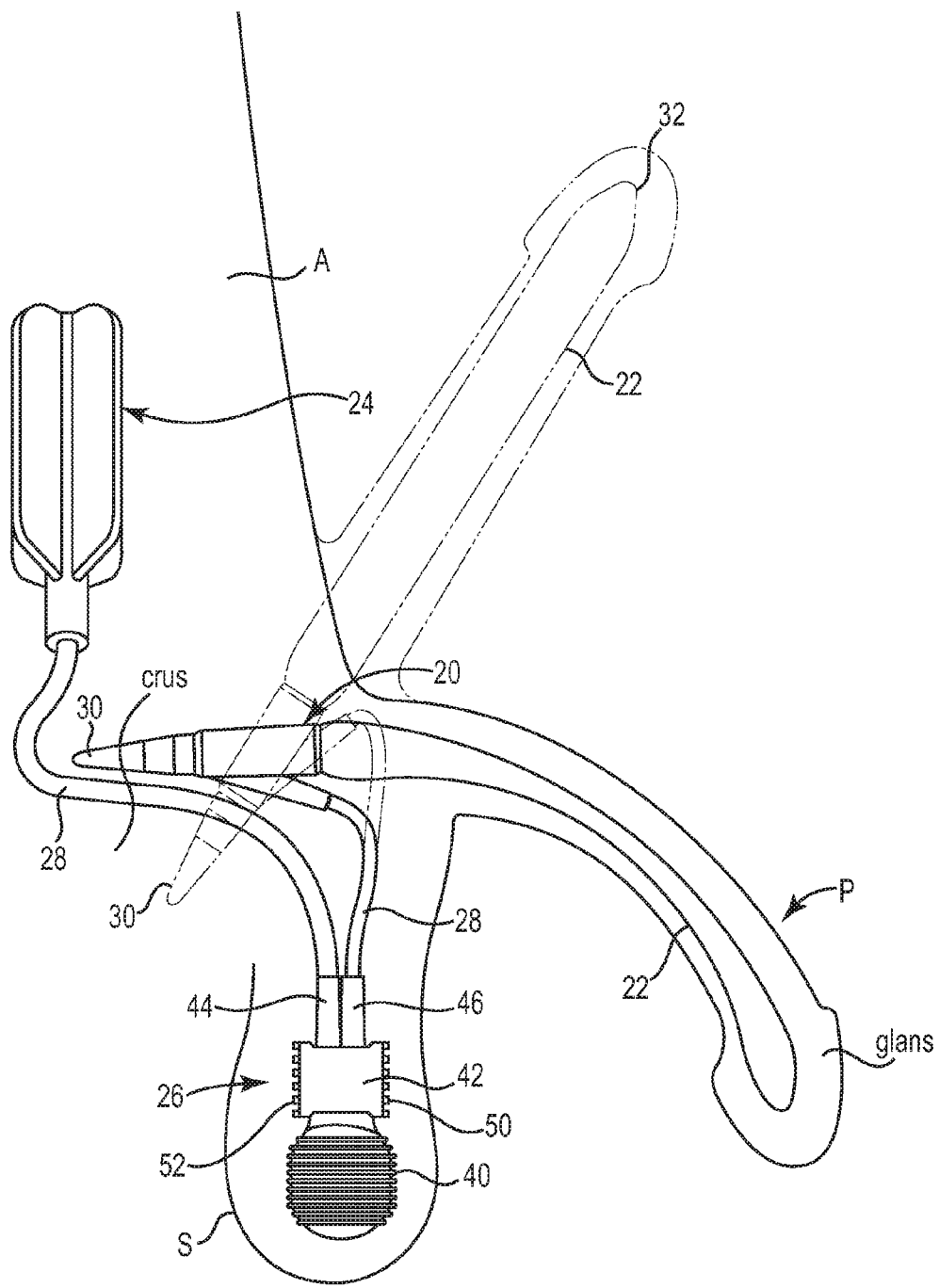
FIG. 9 is a schematic view of one embodiment of the penile prosthetic illustrated in FIG. 1 implanted into a user.

For example, in one embodiment the spring 98 the AAI valve 60 biases the seal 96 to close a potential fluid pathway from the reservoir 24 to the cylinders 22 that would bypasses the pump bulb 40. In one embodiment, the seal 96 is a conical seal having a greater surface area on the wide end 107 (FIG. 4B) that is oriented toward the reservoir 24, such that fluid flow from the reservoir 24 forces the seal 96 into sealing contact with a surface FIG. 9 is a schematic side view of the penile prosthetic 20 implanted in a user. The cylinders 22 are implanted in the penis P with the proximal end 30 inserted near the crus and the distal end 32 implanted within the glans. The reservoir 24 is implanted within the abdomen A and the pump 26 is implanted within the scrotum S. The penile prosthetic 20 is operable consistent with the description above to inflate the cylinders 22 such that the penis P achieves an erect state (as described relative to FIG. 6). The cylinders 22 are configured to deflate to return the penis P to a flaccid state (as described relative to FIG. 7).

In one embodiment, the pump 26 provides a one-touch release mechanism that allows the cylinders 22 to easily and quickly deflate by an initial, nearly instantaneous activation of the surfaces 50, 52 as opposed to the user applying prolonged pressure (e.g., more than three seconds of applied pressure) to the surfaces 50, 52. Thus, a quick and convenient approach is provided for the rapid deflation of the inflated cylinders 22.

In one embodiment, the inlet valve assembly 54, the exhaust valve assembly 56, and the deflation valve 60 have this sequence of inflation operations: The Penis P is flaccid and reservoir 24 is filled. The inlet valve assembly 54 is closed, the exhaust valve assembly 56 is closed, and the deflation valve 60 is closed. The pump bulb 40 is squeezed, the valve 70 is closed against the entry valve seat 72 of the inlet valve assembly 54, and the exhaust valve assembly 56 opens to allow fluid flow and is biased closed to cease flow. The deflation valve 60 is closed and remains closed during subsequent pumping of the pump bulb 40, and fluid flows from the pump bulb 40 through the exhaust valve assembly 56 to the penile cylinder(s) 22. When the pump bulb 40 is released during pumping action, the bulb volume expands to create suction and fluid is drawn from the reservoir 24, all the way through the inlet valve assembly 54, across both seats 72, 73, to the pump bulb 40. The exhaust valve is closed when the pump bulb 40 is released during pumping action and the deflation valve 60 is closed until the bulb 40 is squeezed. Squeezing the bulb 40 ejects the fluid from the bulb 40 and through the exhaust valve assembly 56.

In one embodiment, the inlet valve assembly 54, the exhaust valve assembly 56, and the deflation valve 60 have this sequence of deflation operations: The penis P is erect and the cylinder(s) 22 are filled. The inlet valve assembly 54 is closed, the exhaust valve assembly 56 is closed, and the deflation valve 60 is closed. The surfaces 50, 52 are pushed to open the deflation valve 60 and the liquid flows from the penile cylinder(s) 22 transversely through the deflation valve 60 and the pump body 42 to the reservoir 24 while the inlet valve assembly 54 is closed and the exhaust valve assembly 56 is closed. The tubular sleeve 76 is provided as a component of the inlet valve assembly 54 to ensure that high-pressure fluid flowing from the cylinders 22 and a reservoir 24 will not flow through the inlet channel 55 and give rise to fluid recirculation that has the potential to undesirably close the deflation valve 60.

In one embodiment, the inlet valve assembly 54, the exhaust valve assembly 56, and the deflation valve 60 have this sequence of anti-autoinflation operations: The penis P is flaccid and the reservoir 24 is filled with fluid. The inlet valve assembly 54 is closed, the exhaust valve assembly 56 is closed, and the deflation valve 60 is closed. The reservoir 24 is pressurized, either through a natural body function (e.g., sneezing) or through an external force (e.g., the user pressing against a table edge). The seal 96 of the deflation valve 60 functioning as an AAI valve remains closed and prevents fluid flow from bypassing the pump bulb 40 and flowing from the reservoir 24 to the cylinders 22.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of medical devices as discussed herein. Therefore, it is intended that this invention be limited only by the claims and the equivalents thereof.

What is claimed is:

1. A pump connected to a reservoir and a cylinder of an implantable penile prosthesis, the pump comprising:
   a pump body and a pump bulb that is connected to the pump body, the pump bulb operable to move fluid between the reservoir and the cylinder; and
   an inlet valve assembly comprising a valve and a tubular sleeve that provides an exit valve seat, the inlet valve assembly disposed in an inlet channel of the pump body and operable to allow a portion of fluid to be drawn from the reservoir through the tubular sleeve and through the inlet channel to the pump bulb for delivery into the cylinder;
   wherein the inlet channel of the pump body provides an entry valve seat, and the valve of the inlet valve assembly is movable between the entry valve seat and the exit valve seat.

2. The pump of claim 1, further comprising:
   an exhaust valve assembly disposed in the pump body and operable to allow the portion of the fluid delivered into the pump bulb to be moved into the cylinder.

3. The pump of claim 1, wherein the valve is movable to contact the exit valve seat and prevent fluid that is flowing from the cylinder to the reservoir from flowing through the inlet channel.

4. The pump of claim 1, wherein the tubular sleeve is axially aligned with a spring.

5. The pump of claim 4, wherein the tubular sleeve is disposed inside of the spring and a proximal end of the spring is seated against the flange.

6. The pump of claim 1, further comprising:
   a deflation valve disposed in the pump body, the deflation valve having an open deflate position that selectively allows pressurized fluid to flow from the cylinder to the reservoir;
   wherein the valve of the inlet valve assembly is movable to plug the tubular sleeve and the inlet channel to prevent flowing pressurized fluid from closing the deflation valve.

7. The pump of claim 6, wherein the deflation valve is disposed in the pump body transverse to the inlet valve assembly and the exhaust valve assembly.

8. The pump of claim 6, wherein the pressurized fluid is pressurized to a pressure greater than 8 psi, and the valve of the inlet valve assembly is sized to plug the tubular sleeve to prevent the flowing pressurized fluid from creating fluid recirculation forcing the deflation valve into a closed position.

9. The pump of claim 1, wherein the implantable penile prosthesis includes two cylinders connected to the pump body by two exhaust tubes that are in fluid communication with the reservoir.

10. A penile prosthetic system comprising:
    a cylinder implantable into a penis;
    a reservoir;
    a pump body and a pump bulb that is connected to the pump body, the pump bulb operable to move fluid between the reservoir and the cylinder;
    an inlet valve assembly disposed in an inlet channel of the pump body and operable to allow a portion of the fluid to be drawn from the reservoir through the inlet channel and delivered into the pump bulb; and
    an exhaust valve assembly disposed in the pump body and operable to allow the portion of the fluid delivered into the pump bulb to be moved into the cylinder;
    wherein the inlet valve assembly is responsive to a first pressure to allow the fluid to be drawn from the reservoir and delivered into the pump bulb and responsive to a second pressure greater than the first pressure to prevent fluid flowing from the cylinder to the reservoir from passing through the inlet channel;
    wherein the inlet valve assembly comprises a valve that is movable between an entry valve seat and an exit valve seat of the inlet valve assembly, the valve configured to seal against the exit valve seat to prevent fluid flowing from the cylinder to the reservoir from passing the inlet valve.

11. The penile prosthetic system of claim 10, wherein the inlet valve assembly comprises a tubular sleeve that is disposed inside of the spring, with a distal end of the tubular sleeve providing the exit valve seat.

12. The penile prosthetic system of claim 11, wherein the tubular sleeve comprises a proximal end that is provided with a flange extending in a radial direction from the tube.

13. The penile prosthetic system of claim 12, wherein the flange is disposed between a wall of the pump body and the spring.

14. The penile prosthetic system of claim 10, further comprising:
 a deflation valve disposed in the pump body transverse to the inlet valve assembly and the exhaust valve assembly.

\* \* \* \* \*